United States Patent
Yaginuma

(10) Patent No.: US 10,976,328 B2
(45) Date of Patent: Apr. 13, 2021

(54) STORAGE APPARATUS STORING SPECIMEN CONTAINER AND EXAMINATION SYSTEM USING THE SAME

(71) Applicant: TOSHIBA TEC KABUSHIKI KAISHA, Tokyo (JP)

(72) Inventor: Jun Yaginuma, Shizuoka (JP)

(73) Assignee: TOSHIBA TEC KABUSHIKI KAISHA, Tokyo (JP)

(*) Notice: Subject to any disclaimer, the term of this patent is extended or adjusted under 35 U.S.C. 154(b) by 454 days.

(21) Appl. No.: 15/903,102

(22) Filed: Feb. 23, 2018

(65) Prior Publication Data
US 2018/0238920 A1    Aug. 23, 2018

(30) Foreign Application Priority Data
Feb. 23, 2017 (JP) ............... JP2017-032082

(51) Int. Cl.
| G01N 1/00 | (2006.01) |
| G01N 35/00 | (2006.01) |
| G16H 10/40 | (2018.01) |
| B01L 3/00 | (2006.01) |
| B01L 9/06 | (2006.01) |

(52) U.S. Cl.
CPC ...... *G01N 35/00732* (2013.01); *B01L 3/5453* (2013.01); *B01L 9/06* (2013.01); *G16H 10/40* (2018.01); *B01L 3/50* (2013.01); *B01L 2300/02* (2013.01); *B01L 2300/022* (2013.01); *B01L 2300/023* (2013.01); *G01N 2035/00782* (2013.01)

(58) Field of Classification Search
None
See application file for complete search history.

(56) References Cited

U.S. PATENT DOCUMENTS 5,641,634 A * 6/1997 Mandecki ............ C12Q 1/6825
340/10.3
7,718,442 B2 * 5/2010 Davis ...................... A01N 1/02
422/561

FOREIGN PATENT DOCUMENTS

| JP | 2005-009863 | 1/2005 |
| JP | 2005-125144 | 5/2005 |
| JP | 2006-115330 | 4/2006 |
| JP | 2010-155242 | 7/2010 |
| JP | 2014-190864 | 10/2014 |
| JP | 2017-027345 | 2/2017 |

OTHER PUBLICATIONS

Japanese Office Action for Japanese Patent Application No. 2017-032082 dated Jan. 5, 2021.

* cited by examiner

*Primary Examiner* — Jyoti Nagpaul
(74) *Attorney, Agent, or Firm* — Amin, Turocy & Watson, LLP

(57) ABSTRACT

There is provided a storage apparatus including a storage case which stores a specimen container accommodating a specimen inside and having a wireless tag recorded with identification information on a side surface, and an antenna surrounding the periphery of the specimen container stored in the storage case.

13 Claims, 7 Drawing Sheets

STORAGE APPARATUS STORING SPECIMEN CONTAINER AND EXAMINATION SYSTEM USING THE SAME

CROSS-REFERENCE TO RELATED APPLICATION

This application is based upon and claims the benefit of priority from Japanese Patent Application No. P2017-032082, filed Feb. 23, 2017, the entire contents of which are incorporated herein by reference.

FIELD

Embodiments described herein relate generally to a storage apparatus which stores a specimen container that accommodates a specimen such as blood, and an examination system using the storage apparatus.

BACKGROUND

In the related art, for example, blood (specimen) collected from a patient is put into a blood collection tube of which a bar code is attached to a side surface and the blood collection tube is managed by using the bar code associating information on the patient and the blood. However, in this case, it is necessary to arrange the directions of a plurality of the blood collection tubes to be stored in a rack so that the bar codes of the plurality of blood collection tubes stored in the rack can be efficiently read.

Meanwhile, there is known a technique in which a wireless tag such as a Radio Frequency Identification (RFID) tag is attached to a blood collection tube to read and write identification information in a wireless manner. In this manner, by attaching a wireless tag to the blood collection tube, data on the wireless tag can be read and written regardless of the direction of the blood collection tube.

DETAILED DESCRIPTION

Figure 1:
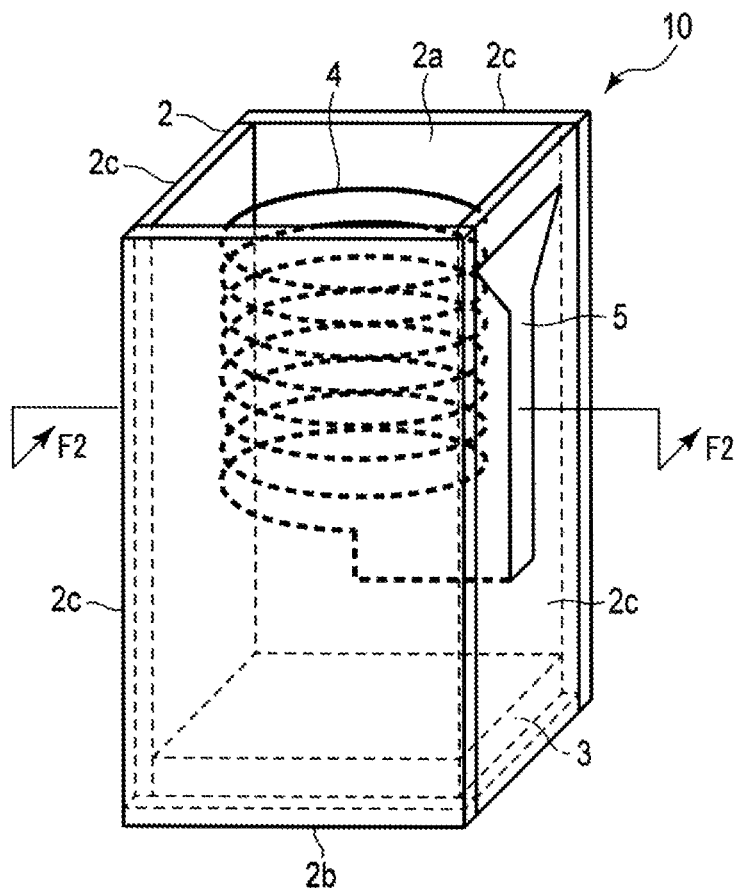
FIG. 1 is a schematic perspective view illustrating a storage apparatus according to a first embodiment.

However, in the method using the above-described wireless tag, in a case where a plurality of blood collection tubes are arranged and stored in a rack, data on a wireless tag of another adjacent blood collection tube may be misread. In order to prevent such problem, a partition wall for shielding radio waves is provided between adjacent blood collection tubes in the apparatus of the related art. However, in a case where a partition wall is provided between the blood collection tubes, there is a need to move an antenna of a reader writer close to each of the wireless tags by avoiding the partition wall to individually read and write data from and to a wireless tag of each blood collection tube. Therefore, it takes labor and the examination time becomes longer.

Accordingly, a development of a storage apparatus which can reliably read and write data from and to a wireless tag in a short period of time regardless of a direction of a specimen container, and an examination system using the storage apparatus is desired.

A storage apparatus according to an embodiment includes a storage portion which stores a specimen container accommodating a specimen inside and having a wireless tag recorded with identification information on a side surface of the specimen container, and a cylindrical antenna which surrounds a periphery of the specimen container stored in the storage portion.

A storage apparatus according to another embodiment includes a plurality of storage portions, each of which stores a specimen container accommodating a specimen inside and having a wireless tag recorded with identification information on a side surface of the specimen container, a plurality of cylindrical antennas, each of which surrounds a periphery of the specimen container stored in each of the storage portions, a plurality of shielding members, each of which shields electromagnetic waves by surrounding an outside of each of the cylindrical antennas, a plurality of insulating members, each of which is disposed between each of the cylindrical antennas and each of the shielding members, a common external antenna which is connected to the plurality of cylindrical antennas and disposed on an outside of the corresponding shielding member, and a plurality of switches, each of which switches a status between connection and disconnection of the plurality of cylindrical antennas and the external antenna.

The specimen is typically blood, but can be any biological material that requires examination. Other examples of biological materials include saliva, urine, a biopsy sample, spinal fluid, stool sample, mucus, pus, sweat, gastric washings, sputum, vaginal fluid, and the like.

An examination system according to still another embodiment includes a plurality of storage portions, each of which stores a specimen container accommodating a specimen inside and having a wireless tag recorded with identification information on a side surface of the specimen container, a plurality of cylindrical antennas, each of which surrounds a periphery of the specimen container stored in each of the storage portions, a plurality of shielding members, each of which shields electromagnetic waves by surrounding an outside of each of the cylindrical antennas, a plurality of insulating members, each of which is disposed between each of the cylindrical antennas and each of the shielding members, a common external antenna which is connected to the plurality of cylindrical antennas and disposed on an outside of the corresponding shielding member, a plurality of switches, each of which switches a status between connection and disconnection of the plurality of cylindrical antennas and the external antenna, a connection unit configured to connect only the cylindrical antenna surrounding a specimen container which accommodates a specimen to be an examination target to the external antenna by switching the plurality of switches, and a data processor which transmits and receives data between a wireless tag of the specimen container and the data processor in a wireless manner via the external antenna, and reads data from the wireless tag and/or writes data to the wireless tag.

Hereinafter, the embodiments will be described in detail with reference to the drawings.

First Embodiment

Figure 2:
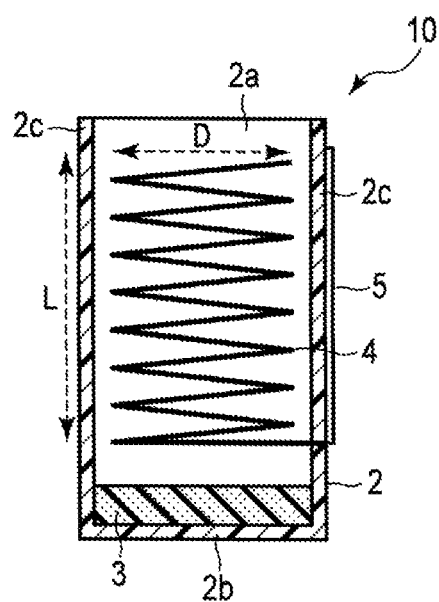
FIG. 2 is a cross sectional view of the storage apparatus in FIG. 1 along line F2-F2.
Figure 3:
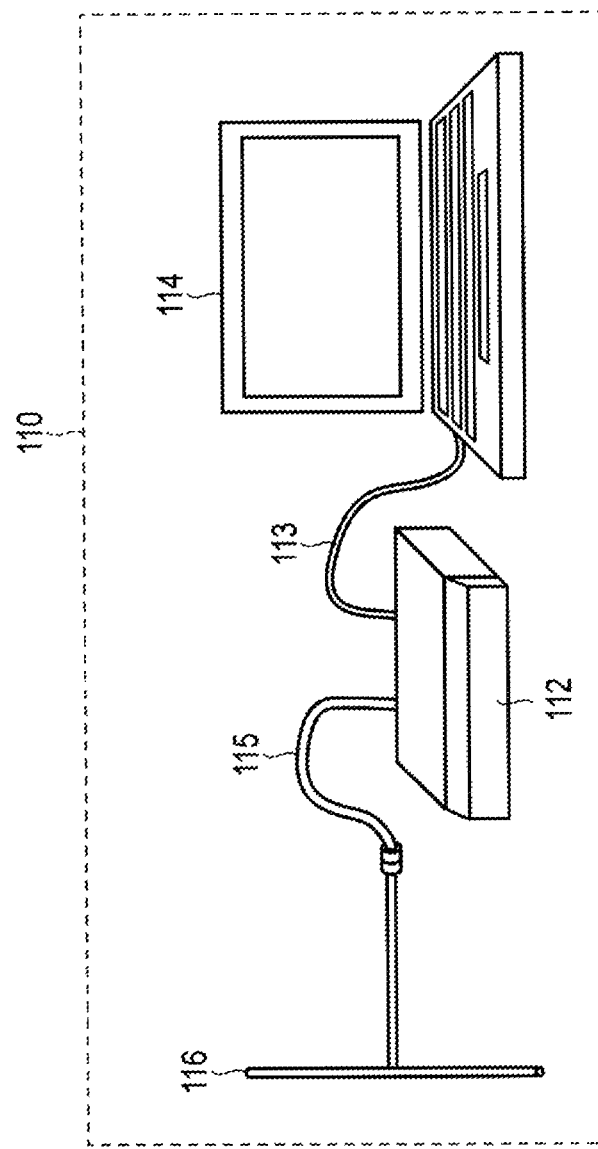
FIG. 3 is a schematic view illustrating an examination system using the storage apparatus in FIG. 1.
Figure 3:
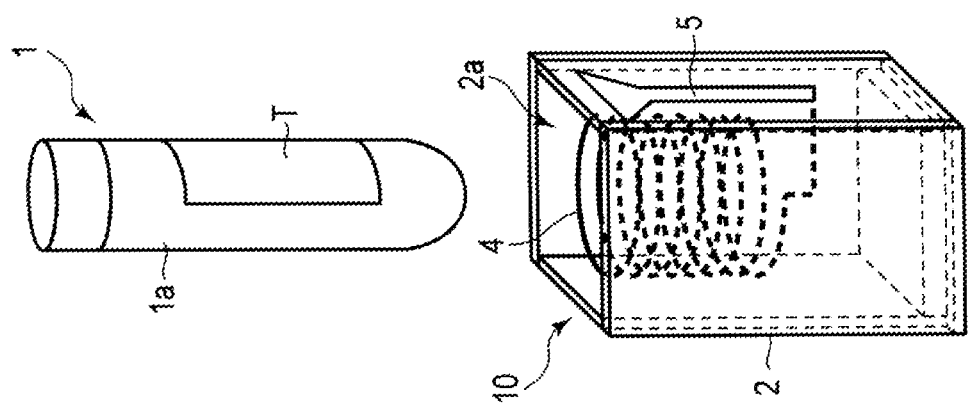

FIG. 1 is a perspective view illustrating a storage apparatus 10 according to a first embodiment, and a side wall 2c on the front side is shown in a transparent manner so that the internal structure can be seen through. FIG. 2 is a cross sectional view illustrating the storage apparatus 10 in FIG. 1 along line F2-F2. FIG. 3 is a schematic view illustrating an examination system 100 using the storage apparatus 10.

As illustrated in FIGS. 1 and 2, the storage apparatus 10 has a rectangular box-shaped storage case 2 (storage portion) having an open upper end. The storage case 2 has a rectangular bottom wall 2b, and four rectangular side walls 2c. The storage case 2 is formed of, for example, resin. A rectangular plate-shaped impact absorber 3 is disposed on the bottom wall 2b of the storage case 2. The impact absorber 3 absorbs impact when a lower end of the specimen container 1 (FIG. 3) described below comes into contact.

As illustrated in FIG. 3, the storage case 2 stores the specimen container 1 accommodating a specimen such as blood. A specimen is not limited to blood or fluid. The specimen container 1 is formed of, for example, a bottomed cylindrical transparent glass tube, and various sizes of tubes are prepared in accordance with the type of the specimen.

A Radio Frequency Identification (RFID) tag T (hereinafter, referred to as wireless tag T) is attached to the side surface of the specimen container 1. The wireless tag T includes an IC chip (not shown) to record data related to identification information of the specimen, and an antenna (not shown) for transmitting and receiving a wireless signal to read and write the data from and to the IC chip. Various information such as identification information of a specimen can be printed on the surface of the wireless tag T. For example, in a case where the specimen is blood, the identification information of the specimen includes information such as a name and an examination date of a patient.

The storage apparatus 10 includes a coil-shaped antenna 4 (cylindrical antenna) inside the storage case 2. The antenna 4 is disposed at a position around the specimen container 1, inserted from an upper end opening 2a of the storage case 2. The antenna 4 according to the embodiment is formed by winding a conductor such as metal in a coil shape, and is to surround the entire circumference of the specimen container 1 in a state where the lower end of the specimen container 1 abuts the impact absorber 3 by being inserted into the storage case 2.

The antenna 4 may be disposed at a position where at least a wireless tag T overlaps the antenna, and there is no need for the antenna to be provided over the entire length of the specimen container 1. Moreover, the storage case 2 does not need to have a height to store the entire length of the specimen container 1, and is desirable to have a height so that the printed information on the wireless tag T attached to the side surface 1a of the specimen container 1 can be externally visible.

The antenna 4 is not limited to a coil shape, and any shape, such as so-called a cylindrical shape, may be used as long as it surrounds the entire circumference of the specimen container 1. Here, the term "cylindrical shape" means a structure continuous in the circumferential direction to surround the entire circumference of the specimen container 1.

The antenna 4 is for performing reading and writing data in a wireless manner from and to the wireless tag T described below, which is attached to the side surface 1a of the specimen container 1. As illustrated in FIG. 3, the wireless tag T is attached to the side surface 1a of the specimen container 1. That is, the antenna 4 is provided at at least a position that the antenna 4 and the wireless tag T of the specimen container 1 overlap and oppose each other. The inner diameter of the antenna 4 is slightly larger than the outer diameter of the specimen container 1. In one embodiment, the inner diameter of the antenna is 1% or more larger than the outer diameter of the specimen container. In another embodiment, the inner diameter of the antenna is 5% or more larger than the outer diameter of the specimen container. The length L of the antenna 4 is determined by the outer diameter D of the antenna 4 and frequency of the wireless tag T for use.

For example, a blood collection tube accommodating blood collected from a patient has an outer diameter of approximately 12 mm to 16 mm. The outer diameter D of the antenna 4 suitable for such a blood collection tube is approximately 16 mm to 18 mm. In a case where the wireless tag T attached to the blood collection tube operates in the UHF band (920 MHz band in Japan), the length L of the antenna 4 may be approximately 65 mm. That is, the antenna 4 is disposed near the periphery of the specimen container 1.

A coupler 5 is provided for relaying signals from a reader writer 112 (FIG. 3) described below in a contactless manner on the outside of the storage case 2. The coupler 5 is attached to the outer surface of one of the side walls 2c of the storage case 2. The coupler 5 is connected to the antenna 4 by a conducting wire penetrating through the corresponding side wall 2c.

As illustrated in FIG. 3, the examination system 100 includes a data processor 110 for performing writing data to the wireless tag T of the specimen container 1 stored in the above-mentioned storage apparatus 10 and/or reading data from the wireless tag T. An IC chip for recording identification information for identifying a specimen in the specimen container 1 is incorporated in the wireless tag T attached to the side surface 1a of the specimen container 1.

The data processor 110 includes a reader writer 112, a controller 114, and an antenna 116. The reader writer 112 and the controller 114 are connected to each other via a USB or a LAN cable 113. Moreover, the reader writer 112 and the antenna 116 are connected to each other via a coaxial cable 115.

Figure 4:
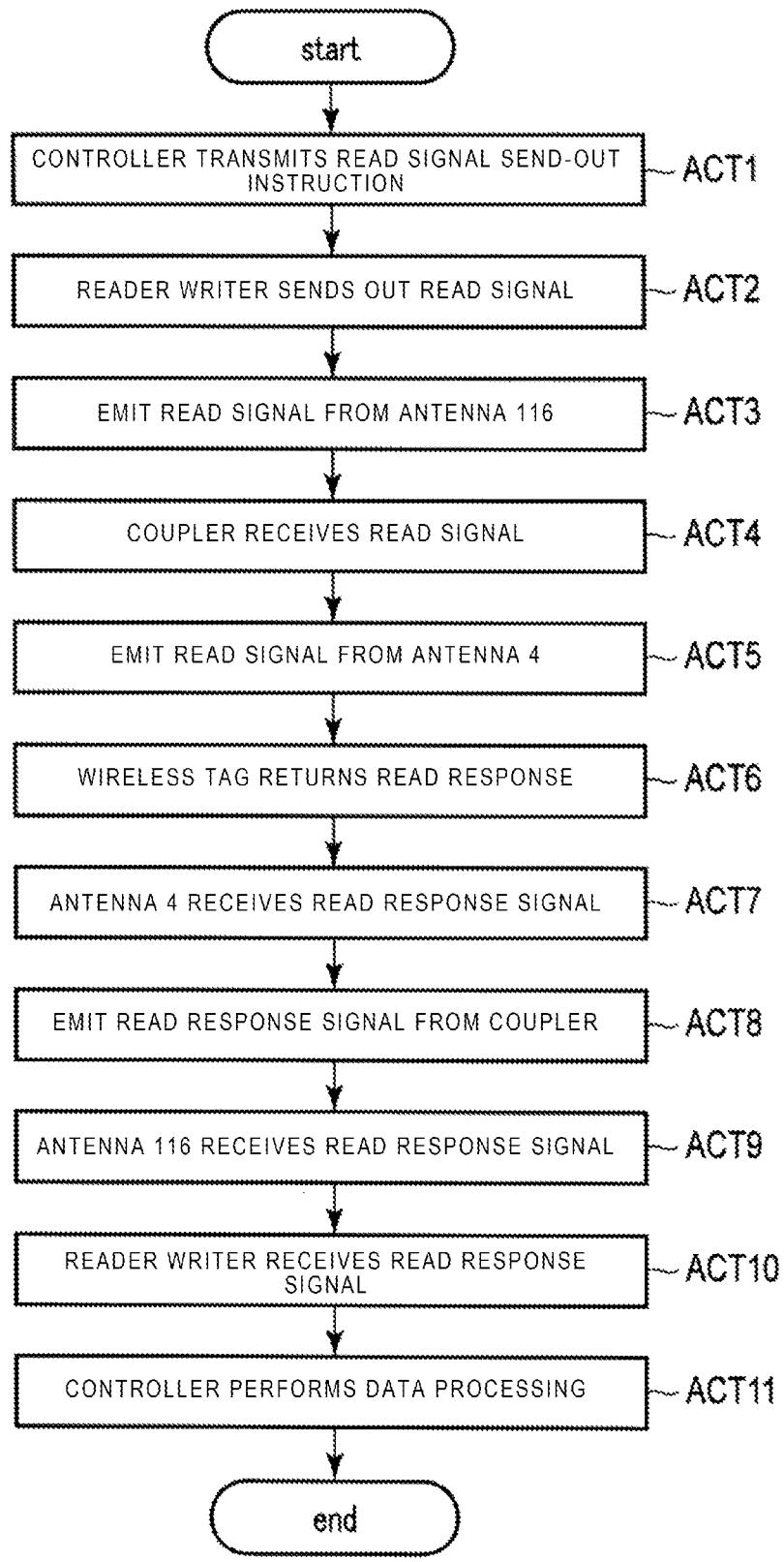
FIG. 4 is a flowchart for explaining a data processing method of the examination system in FIG. 3.

Hereinafter, a data processing method of the examination system 100 in FIG. 3 will be explained with reference to FIG. 4. Here, it is assumed that a specimen container 1 on which a wireless tag T recorded with identification information of a specimen is attached to the side surface 1a is stored in the storage case 2 of the storage apparatus 10.

Firstly, the controller 114 of the data processor 110 transmits an instruction to send out a read signal to the reader writer 112 (ACT 1). The reader writer 112 transmits the read signal (ACT 2) based on the instruction and emits the read signal as a radio wave via the antenna 116 (ACT 3).

The coupler 5 of the storage apparatus 10 receives the radio wave (ACT 4), and transfers the read signal to the antenna 4. The antenna 4 emits the radio wave based on the received read signal (ACT 5). The wireless tag T receives the radio wave related to the read signal and returns a response (ACT 6).

The antenna 4 receives the read response signal from the wireless tag T (ACT 7), and transfers the read response signal to the coupler 5. The coupler 5 emits the read response signal as a radio wave (ACT 8), and the data processor 110 receives the radio wave via the antenna 116 (ACT 9).

The antenna 116 transfers the received read response signal to the reader writer 112 (ACT 10). The reader writer 112 demodulates the received read response signal and transfers the signal to the controller 114. The controller 114 starts the next data processing such as the identification of the examination item from the associated information of ID of the received wireless tag T and a patient (ACT 11).

Next, a design method of the antenna 4 will be described.

In general, when a dielectric approaches an antenna, the resonance frequency shifts to the low frequency side. The antenna 4 according to the embodiment is largely influenced by the insertion of the specimen container 1 inside the antenna 4 as described above. As an example, in a case where an inner diameter D of the antenna 4 is 16 mm, and the outer diameter of the specimen container 1 is 15.8 mm, it is found that the resonance frequency is shifted to the low frequency side, which is approximately 200 MHz, when the material of the specimen container 1 is glass, and the resonance frequency is shifted to the low frequency side, which is approximately 80 MHz, when the material of the specimen container 1 is resin.

For this reason, when designing the antenna 4, it is desirable to design the antenna 4 to function as an antenna at a desired frequency in a state where the specimen container 1 is inserted into the antenna 4. In other words, it is desirable to design the antenna 4 so that the resonance frequency shifted in a state where the specimen container 1 is inserted into the storage apparatus 10 is at a desired frequency.

Alternatively, by making the inner diameter of the antenna 4 to substantially coincide with the outer diameter of the specimen container 1, as described above, it is possible to couple the wireless tag T by the leakage of the magnetic field in addition to the electric field from the antenna 4, and read data from the wireless tag T without depending on the frequency. In this case, it is possible to read and write data from and to the wireless tag T even if the current flowing through the antenna 4 is small. For this reason, it is possible to prevent a problem of misreading data from a wireless tag T attached to another specimen container 1 inside an adjacent storage apparatus 10 and to improve the reading accuracy of the wireless tag T even if a plurality of the storage apparatuses 10 are juxtaposed adjacent to each other.

As described above, in the storage apparatus 10 according to the embodiment, it is possible to reliably read data from the wireless tag T regardless of the inserting direction of the storage case 2 of the specimen container 1, since the coil-shaped antenna 4 is provided so as to cover the entire circumference of the specimen container 1. In other words, even if the directions of the specimen containers 1 to the antenna 4 vary, it is possible to read data from the wireless tag T with the same conditions, and uniformly stabilize the reading accuracy of the wireless tag T.

On the other hand, in a case where data on the wireless tag T of the specimen container 1 is read via the antenna 116 disposed fixedly on one surface side of the storage apparatus without the coil-shaped antenna 4, the positional relationship (relative angle) with the antenna 116 changes according to the direction of the specimen container 1, and a reading defect may occur. In this case, distribution also occurs in the reliability of the reading result according to the direction of the specimen container 1, and reading cannot be performed uniformly and stably.

Accordingly, as in the embodiment, it is desirable to provide the antenna 4 surrounding the entire circumference of the specimen container 1 and realize high reliability in reading data from the wireless tag T regardless of the direction of the specimen container 1.

Second Embodiment

Figure 5:
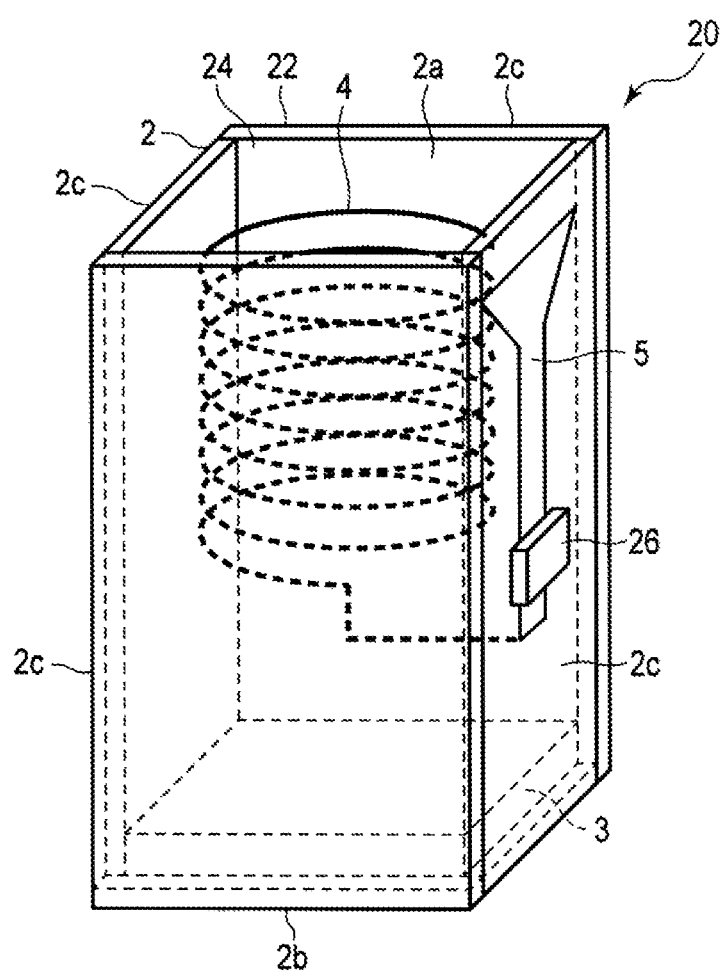
FIG. 5 is a schematic perspective view illustrating a storage apparatus according to a second embodiment.

FIG. 5 is a perspective view illustrating a storage apparatus 20 according to a second embodiment, and is a view corresponding to FIG. 1. Here, the same reference numerals are assigned to components that function in the same manner as in the configuration of FIG. 1 (configuration of the first embodiment), and the detailed description thereof is omitted.

The storage apparatus 20 has a configuration that is assumed to use a plurality of the storage apparatuses 20 juxtaposed adjacent to each other. That is, the storage apparatus 20 includes a shielding layer 22 (shielding member) for shielding the electromagnetic waves outside the antenna 4, and an insulating layer 24 (insulating member) interposed between the antenna 4 and the shielding layer 22. The storage apparatus 20 includes a switching element 26 (switch) that switches the status between connection and disconnection of both the antenna 4 and the coupler 5 (external antenna).

According to the embodiment, the shielding layer 22 is provided so as to cover the entire inner surface of the storage case 2. That is, the shielding layer 22 is provided on the inner surface of the bottom wall 2b of the storage case 2, and each of the inner surfaces of the four side walls 2c. The shielding layer 22 is provided to prevent a leakage of the radio wave emitted from the antenna 4 to the outside of the storage apparatus 20. Therefore, the shielding layer 22 is not limited to the inner surface of the storage case 2, and may be provided so as to cover the outside of the antenna 4, such as the outer surface of the storage case 2.

The antenna 4 emits radio waves for reading data from the wireless tag T attached to the side surface 1a of the specimen container 1. Accordingly, the radio wave emitted from the antenna 4 may be leaked to the outside of the storage apparatus 20, in a case where the shielding layer 22 is not provided. Therefore, when a plurality of the storage apparatuses 20 without the shielding layer 22 are disposed close to each other, data on another wireless tag T of the specimen container 1 stored in the adjacent storage apparatus 20 may be misread.

For this reason, in a case where a plurality of the storage apparatuses 20 are disposed close to each other, as in the embodiment, it is desirable to provide the shielding layer 22 outside the antenna 4 to suppress the leakage of radio waves. The shielding layer 22 is formed of a conductive member and a sheet of a metal film or the like is used. Although the shielding layer 22 is used in the embodiment, a radio wave absorber or the like having a similar function may be used instead of the shielding layer 22.

In the embodiment, the insulating layer 24 is stacked on the inner surface of the shielding layer 22 so as to cover the entire inner surface of the shielding layer 22. The antenna 4 and the shielding layer 22 are formed with a conductive member, and the antenna 4 may not function properly when the antenna and the shielding layer are in contact. Therefore, the insulating layer 24 is stacked on the inner surface of the shielding layer 22. The insulating layer 24 may be provided between the shielding layer 22 and the antenna 4, and is not necessarily to be provided on the inner surface of the shielding layer 22.

A switching element 26, for example, is a reed switch, and switches between transmission and non-transmission status of a signal between the antenna 4 and the coupler 5 by a magnetic field. As a method for applying the magnetic field, a method of approaching a magnet (not shown) to the switching element 26 is considered. By providing the switching element 26 between the antenna 4 and the coupler 5, it is possible to selectively read data only from the wireless tag T of the specimen container 1 stored in a specific storage apparatus 20, even if a plurality of the storage apparatuses 20 are juxtaposed adjacent to each other.

As described above, in the storage apparatus 20 according to the embodiment, even if the plurality of storage apparatuses 20 are juxtaposed adjacent to each other, it is possible to selectively read data only from the wireless tag T of the specimen container 1 stored in the specific storage apparatus 20, and improve reliability of the data processing.

Third Embodiment

Figure 6:
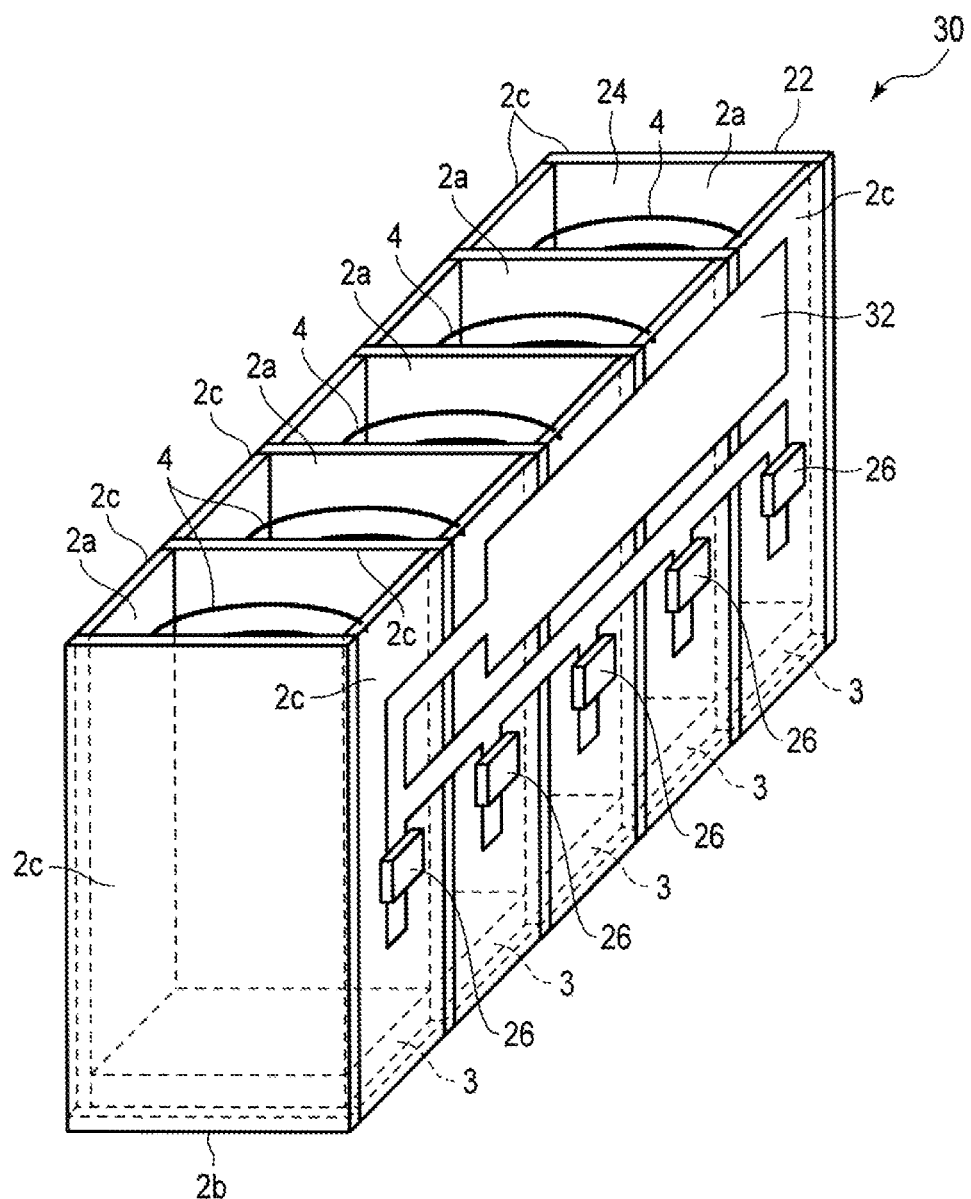
FIG. 6 is a schematic perspective view illustrating a storage apparatus according to a third embodiment.
Figure 7:
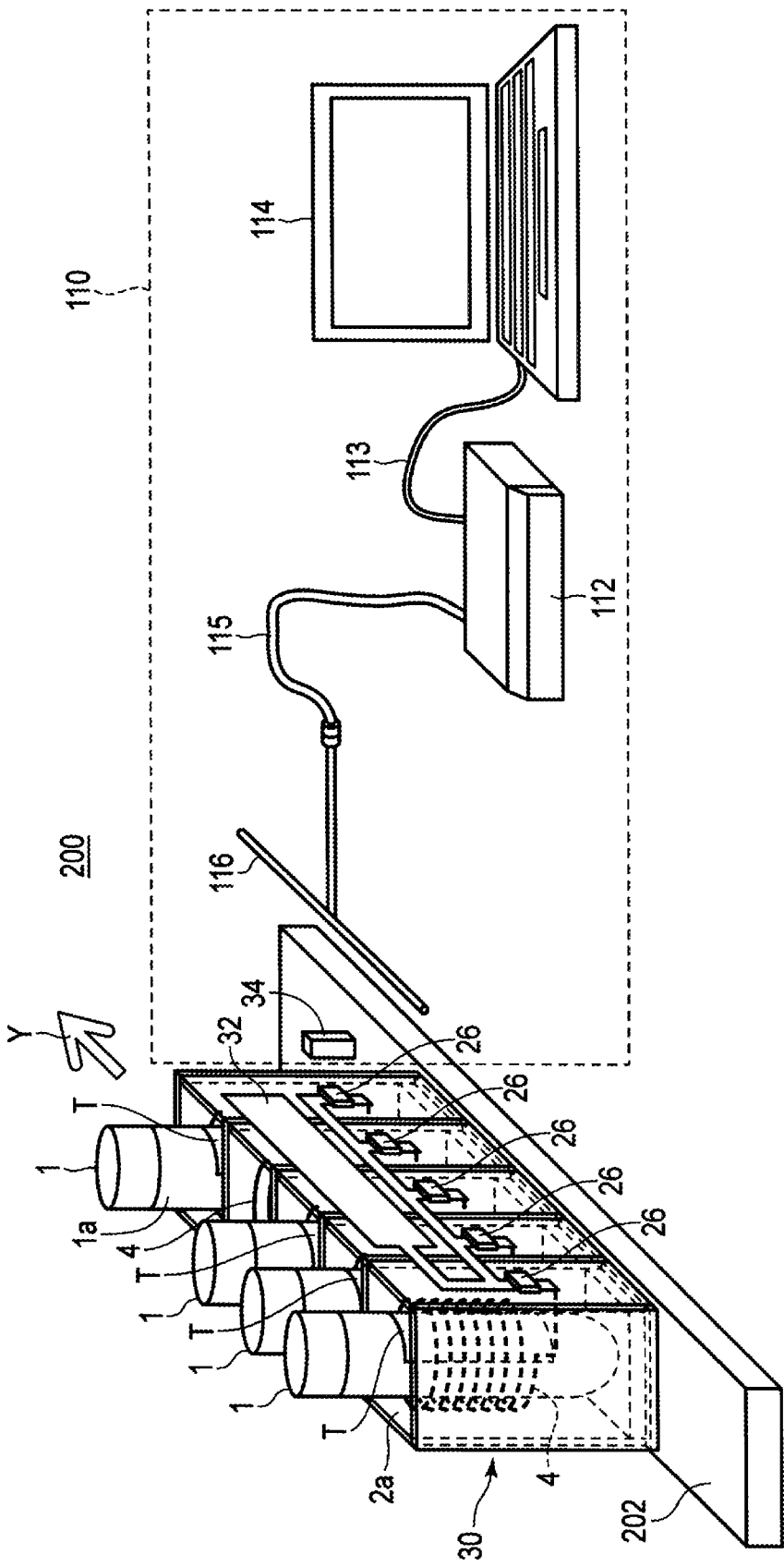
FIG. 7 is a schematic view illustrating an examination system using the storage apparatus in FIG. 6.

FIG. 6 is a perspective view illustrating a storage apparatus 30 according to a third embodiment, and FIG. 7 is a schematic view illustrating an examination system 200 using the storage apparatus 30. The storage apparatus 30 generally has a structure in which the storage apparatuses 20 of the second embodiment are connected in a row, and the examination system 200 has a movable stage 202 for placing and moving the storage apparatus 30. The other configurations are substantially the same as those of the examination system 100 of the first embodiment and the storage apparatus 20 of the second embodiment described above. Therefore, here, the components that function in the same manner as the first and the second embodiments described above are denoted by the same reference numerals, and the detailed description thereof is omitted.

As illustrated in FIG. 6, the storage apparatus 30 has a structure in which the storage apparatuses 20 of the second embodiment described above are juxtaposed and connected in a row. According to the embodiment, five storage apparatuses 20 are juxtaposed and connected in a row in a direction in which the switching elements 26 are disposed on the same surface side. Therefore, the storage apparatus 30 of the embodiment can store five specimen containers 1. However, the number of the storage case 2 capable of storing the specimen container 1 is not limited to five, and the number can be arbitrarily changed by changing the number of the connected storage apparatuses 20.

A partition wall between the two adjacent storage apparatuses 20 is a wall sharing one of the side wall 2c with, and the number of the side walls 2c is reduced. A plurality of the couplers 5 provided on the outer surfaces of different side walls 2c of the respective storage apparatuses 20 are gathered together in one of couplers 32 (external antenna). Moreover, an impact absorber 3 is disposed at the bottom of each of the storage cases 2, and the antenna 4 is disposed in each of the storage cases 2. A shielding layer 22 is provided on the inner surface of each of the storage cases 2, and the insulating layer 24 is provided on each of the inner sides of the shielding layers 22.

As illustrated in FIG. 7, the examination system 200 has a data processor 110 and the movable stage 202 described above, in addition to the above-described storage apparatus 30. The storage apparatus 30 is disposed on the movable stage 202, and the movable stage moves at a constant speed in Y direction indicated by an arrow (juxtaposing direction of plurality of storage apparatuses 20). The examination system 200 has a magnet 34 for switching the status between on and off of the five switching elements 26 juxtaposed in a row along an outer surface of one side wall of the storage apparatus 30. The magnet 34 is fixedly disposed at a height position where a plurality of the switching elements 26 are moved, the magnet 34 is individually disposed to sequentially face each of the switching elements 26 by the movable stage 202 moving the storage apparatus 30 in the direction of the arrow Y.

The magnetic force, size, position and the like of the magnet 34 are determined according to the characteristics of the switching element 26 so that only the opposed switching element 26 is turned ON. In order to restrict the magnetic field along the direction of the arrow Y to a narrow area, a switching area may be restricted by providing a metal plate or the like on both the sides of the magnet 34. However, only the switching element 26 facing the magnet 34 is turned ON, and only the antenna 4 of the storage apparatus 20 having the switching element 26 is connected to a coupler 32.

That is, the movable stage 202 which moves the storage apparatus 30 in the direction of the arrow Y and the magnet 34 function as a connection unit configured to connect only the antenna 4 surrounding the specimen container 1 accommodating the specimen to be examined to the coupler 32.

Figure 8:
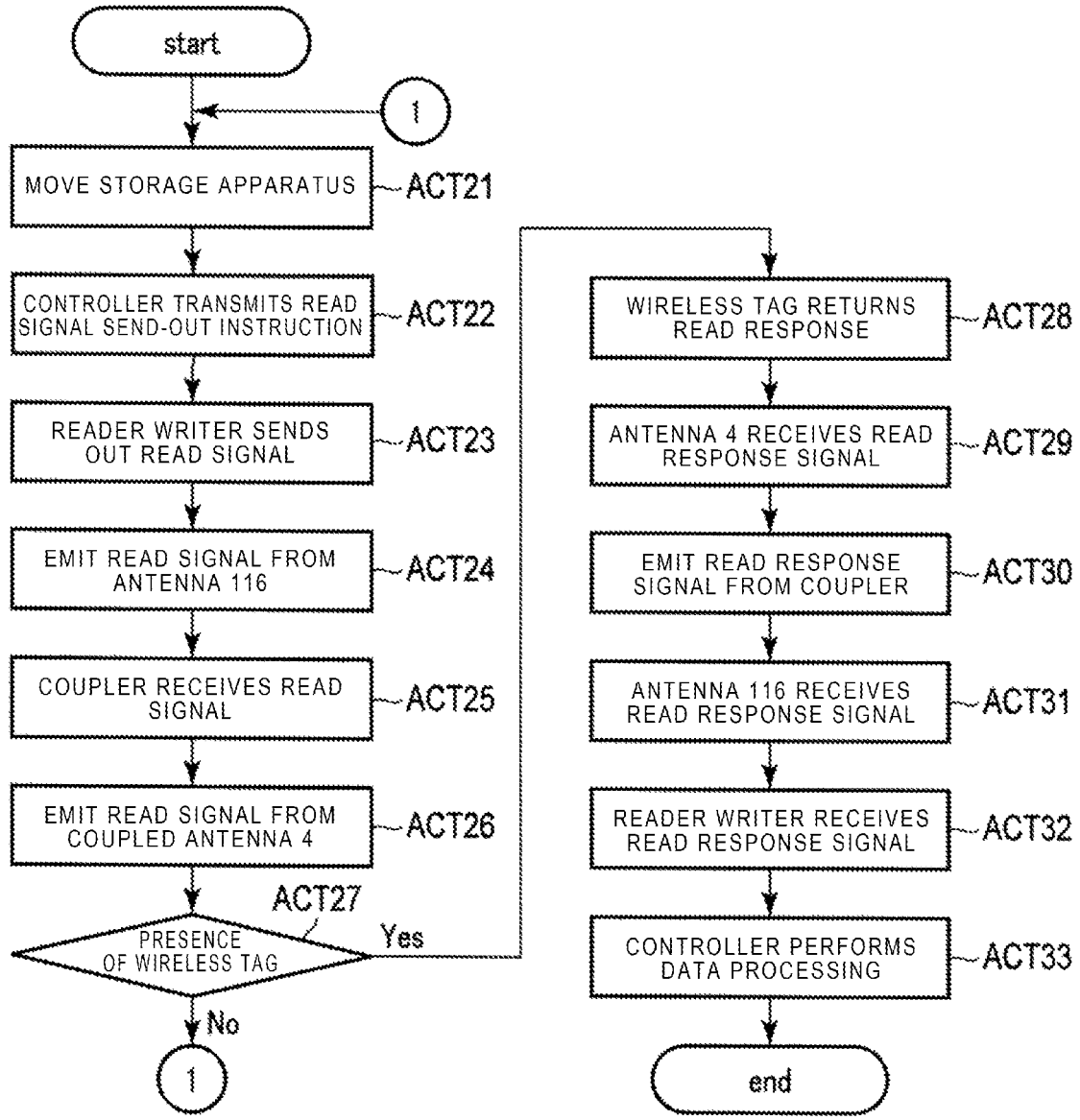
FIG. 8 is a flowchart explaining a data processing method of the examination system in FIG. 7.

Hereinafter, a data processing method of the examination system 200 in FIG. 7 will be explained with reference to FIG. 8. Here, it is assumed that the specimen container 1 is stored in the four storage cases 2 other than the second storage case 2 from the top of the moving direction among the five storage cases 2. That is, the specimen container 1 is not stored in the second storage case 2 from the top.

The examination system 200 controls the movable stage 202 firstly and moves the storage apparatus 30 to a predetermined position (ACT 21). Here, the switching element 26 of the top storage case 2 along the direction of the arrow Y moves the storage apparatus 30 to a position facing the magnet 34.

In this state, the controller 114 of the data processor 110 transmits an instruction to send out a read signal to the reader writer 112 (ACT 22). The reader writer 112 transmits the read signal (ACT 23), and emits the read signal as radio waves via the antenna 116 (ACT 24) based on the instruction.

The common coupler 32 of the storage apparatus 30 receives the radio wave (ACT 25), and transfers the read signal to the antenna 4. At this time, in ACT 21, only the switching element 26 facing the magnet 34 is turned ON, and only the antenna 4 in the top storage case 2 is connected to the coupler 32, so that the read signal is transferred to the antenna 4 in the top storage case 2. The antenna 4 emits radio waves based on the received read signal (ACT 26).

As described above, in a case where the specimen container 1 is stored in the storage case 2 in which the antenna 4 is coupled with the coupler 32 (YES in ACT 27), the wireless tag T attached to the specimen container 1 receives the read signal and returns a response (ACT 28). The antenna 4 of the storage case 2 receives the read response signal from the wireless tag T (ACT 29), and transfers the read response signal to the coupler 32.

The coupler 32 emits the read response signal as a radio wave (ACT 30), and the data processor 110 receives the radio waves via the antenna 116 (ACT 31). The antenna 116 transfers the received read response signal to the reader writer 112 (ACT 32). The reader writer 112 demodulates the received read response signal, and transfers the signal to the controller 114.

The controller 114 starts the next data processing such as the identification of the examination item from the associated information of ID of the received wireless tag T and a patient (ACT 33). After reading data from the wireless tag T of the specimen container 1 in the top storage case 2, the examination system 200 controls the movable stage 202, causes the switching element 26 of the next storage case 2 to face the magnet 34, and shifts to the processing of ACT 22.

In ACT 27, in a case where the specimen container 1 is not stored in the storage case 2 facing the magnet 34 (NO in ACT 27), the examination system 200 returns to ACT 21, and controls the movable stage 202 to move the storage apparatus 30 to a position where the switching element 26 of the next storage case 2 faces the magnet 34. Determination that the specimen container 1 is not stored in the storage case 2 facing the magnet 34, may be made, for example, from an absence of response from the wireless tag T for a certain time period, or by providing a separate sensor.

As described above, according to the storage apparatus 30 and the examination system 200 of the embodiment, the same effects as those of the first and the second embodiments described above can be achieved. Moreover, accordingly to the embodiment, a defect of misreading data from another wireless tag T of adjacent specimen container 1 in the storage case 2 does not occur because a plurality of the specimen containers 1 can be stored in a juxtaposing manner, and only the antenna 4 surrounding one of the specimen containers 1 can be connected to the coupler 32. According to the embodiment, data processing with high reliability can be performed and data on the wireless tag T of a plurality of the specimen containers 1 can be accurately read in a short period of time.

According to the storage apparatus and the examination system of at least one of the above described embodiments, the cylindrical antenna 4 surrounding the specimen container 1 accommodating the specimen inside is used so that reading and writing the data from and to the wireless tag T can be performed reliably in a short period of time regardless of the direction of the specimen containers 1.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A storage apparatus comprising:
    a plurality of storage portions, each of which stores a specimen container accommodating a specimen inside and having a wireless tag recorded with identification information on a side surface of the specimen container;
    a plurality of cylindrical antennas corresponding to the plurality of storage portions, each of which surrounds a periphery of the specimen container stored in each of the storage portions;
    a plurality of shielding members corresponding to the plurality of storage portions, each of which shields electromagnetic waves by surrounding an outside of each of the cylindrical antennas;
    a plurality of insulating members corresponding to the plurality of storage portions, each of which is disposed between each of the cylindrical antennas and each of the shielding members;
    a common external antenna which is connected to the plurality of cylindrical antennas and disposed on an outside of the corresponding shielding member; and
    a plurality of switches corresponding to the plurality of storage portions, each of which switches a status between connection and disconnection of the plurality of cylindrical antennas and the external antenna.

2. The apparatus according to claim 1, wherein the inner diameter of each antenna is slightly larger than the outer diameter of each corresponding specimen container.

3. The apparatus according to claim 1, wherein the inner diameter of each antenna is 1% or more larger than the outer diameter of corresponding specimen container.

4. The apparatus according to claim 1, wherein the inner diameter of each antenna is 5% or more larger than the outer diameter of corresponding specimen container.

5. The apparatus according to claim 1, wherein each specimen container is a blood container.

6. The apparatus according to claim 1, wherein each cylindrical antenna has a coil shape.

7. An examination system comprising:
    the storage apparatus according to claim 1;
    a connection unit configured to connect only a cylindrical antenna surrounding a specimen container which accommodates a specimen as an examination target to the external antenna by switching the plurality of switches; and
    a data processor which transmits and receives data between a wireless tag of the specimen container and the data processor in a wireless manner via the external antenna, and reads data from the wireless tag and/or writes data to the wireless tag.

8. The examination system according to claim 7, wherein the inner diameter of each antenna is slightly larger than the outer diameter of each corresponding specimen container.

9. The examination system according to claim 7, wherein the inner diameter of each antenna is 1% or more larger than the outer diameter of corresponding specimen container.

10. The examination system according to claim 7, wherein the inner diameter of each antenna is 5% or more larger than the outer diameter of corresponding specimen container.

11. The examination system according to claim 7, wherein each specimen container is a blood container.

12. The examination system according to claim 7, wherein each specimen container is a biological material container.

13. The examination system according to claim 7, wherein each cylindrical antenna has a coil shape.

* * * * *